United States Patent [19]
Milligan

[11] Patent Number: 5,713,833
[45] Date of Patent: Feb. 3, 1998

[54] SEPTUM NERVE STIMULATOR

[76] Inventor: Lee John Milligan, 2291 W. Dry Creek Rd., Littleton, Colo. 80120

[21] Appl. No.: 186,690

[22] Filed: Jan. 26, 1994

[51] Int. Cl.[6] ....................................... A61H 7/00
[52] U.S. Cl. ........................... 601/133; 601/134; 128/848
[58] Field of Search ................... 601/133, 134, 601/135; 128/207.18, 848; 606/157, 199, 204.45, 196

[56] References Cited

U.S. PATENT DOCUMENTS

| | | | |
|---|---|---|---|
| 1,281,487 | 10/1918 | Beshgeturian | 601/133 |
| 1,636,159 | 7/1927 | Unné | 601/133 |
| 4,378,802 | 3/1983 | Ersek | 128/346 |
| 4,384,574 | 5/1983 | Wong | 128/846 |
| 4,549,536 | 10/1985 | Varjabedian | 601/133 |
| 4,592,357 | 6/1986 | Ersek | 128/342 |

FOREIGN PATENT DOCUMENTS

| | | | |
|---|---|---|---|
| 533487 | 12/1920 | France | 601/133 |
| 174607 | 6/1959 | Sweden | 128/207.18 |

*Primary Examiner*—Robert A. Hafer
*Assistant Examiner*—Benjamin K. Koo
*Attorney, Agent, or Firm*—Charles C. Corbin

[57] ABSTRACT

A therapeutic device for being removably retained in a person's nostrils is generally U-shaped and includes a pair of opposing resilient arms insertable within the nostrils and soft spherical surfaces on the free ends of the arms for engaging opposing sides of the nasal septum.

6 Claims, 3 Drawing Sheets

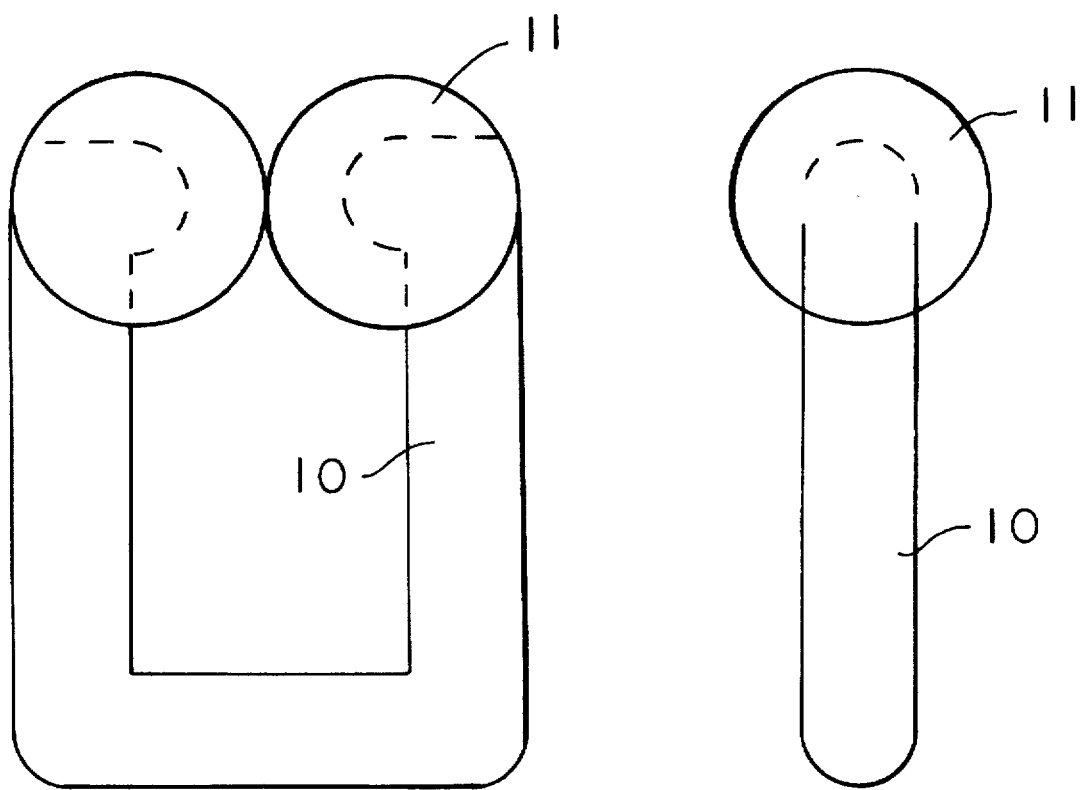

SEPTUM NERVE STIMULATOR

BACKGROUND OF THE INVENTION

The present invention relates to relieving problems associated with the nerves on the septum. The trigeminal nerve provides both sensory and motor fibers. The nerve receives cutaneous, temperature and pressure sensations from different parts of the face head nasal and oral cavities. The nasal septum nerves are one of the recievers. Stimulation of these nerves by controlled pressure could:

1) reduce swelling of nasal passage.

2) reduce dilation of arteries supplying nasal cavities.

3) control secretion from the lacrimal grand above the eye, the palate, mandibular and submandibular gland of the mouth and nasal mucosa.

Application of a pressure to the septum nerve must be controlled automatically so as not to cause irritation, cutting or adverse debilitating pressures. This device allows anyone (without a medical background) to administer the stimulator on the septum.

SUMMARY OF INVENTION

It is the object of the invention to provide a device to safely apply a controlled pressure to the nerves on the septum. The controlled pressure would be designed to conform and distribute said force onto the nose septum nerves. This stimulation could offer relief to breathing and secretion problems.

BRIEF DESCRIPTION OF DRAWINGS

These and further features of the present invention are described in the accompanying drawings in which FIG. 1 is a pictoral (front view) of a septum nerve stimulator which employs the features of the present invention ar rest.

FIG. 2 is a pictoral (side view) of FIG. 1.

FIG. 4. Differs from FIG. 1 in that the force producing member 13 is completely emcompased by a soft material 14.

DESCRIPTION

Figure 3:
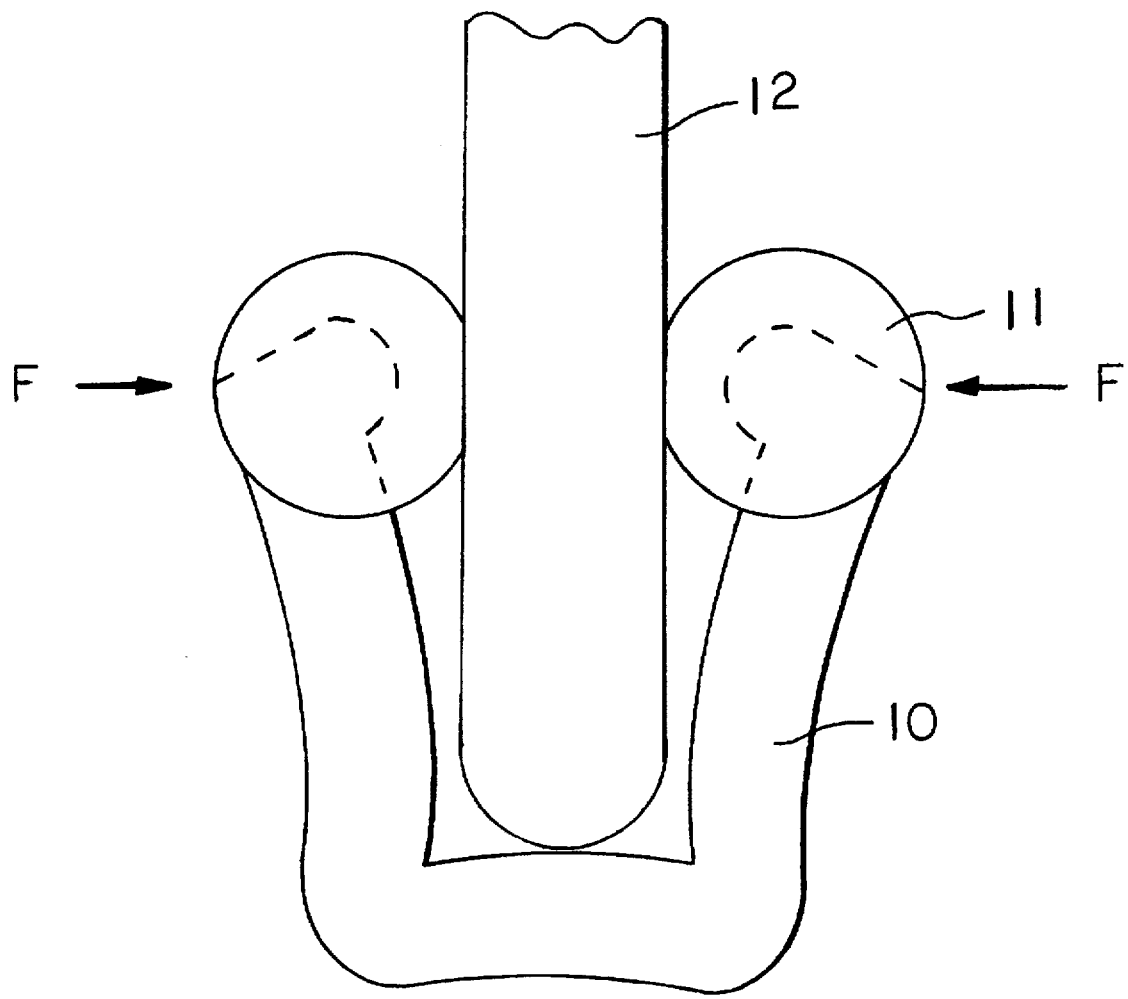
FIG. 3 is a pictoral (front view) of FIG. 1 in the flexed mode.
Figure 4:
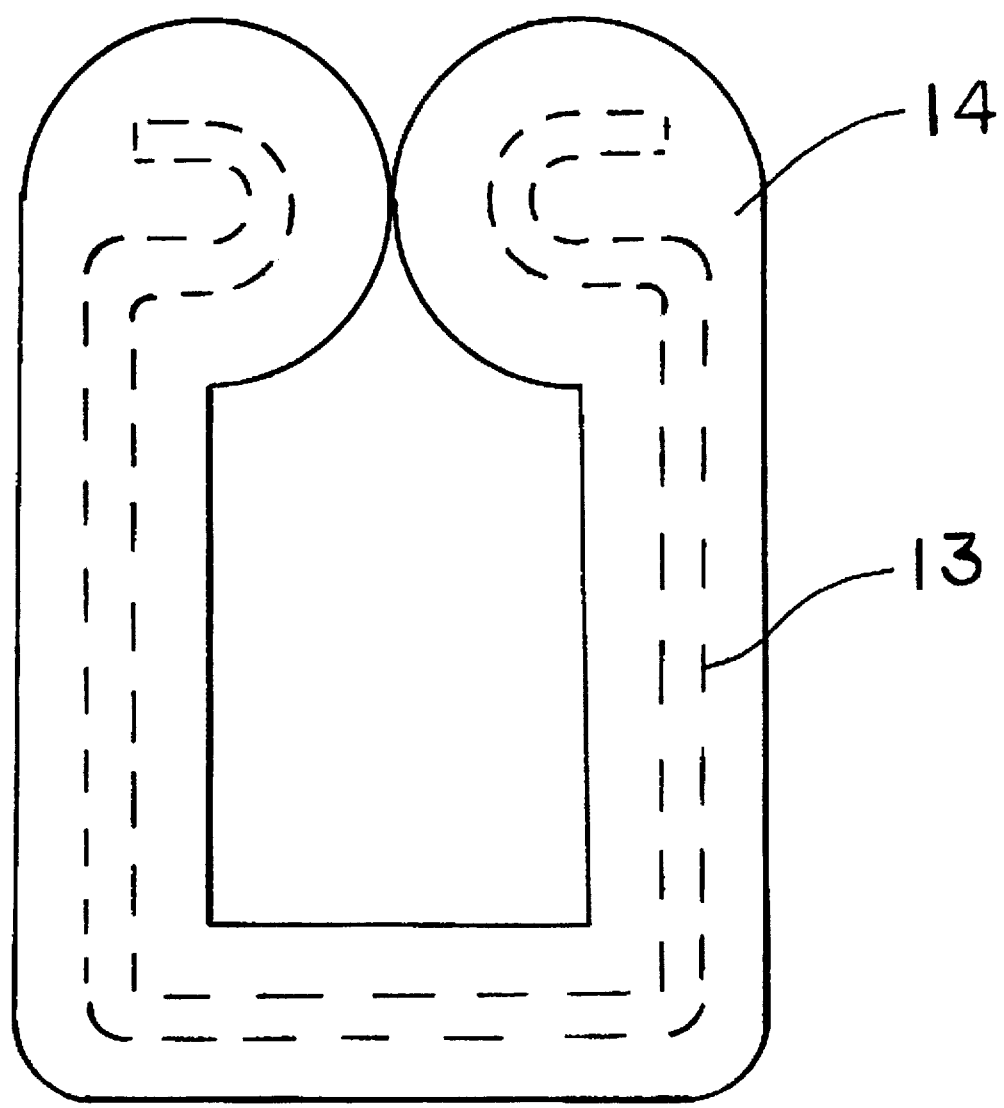
FIG. 4 is a pictoral (front view) of a septum nerve stimulator.

The device as shown in FIG. 1 shows the device in its normal non-flexed mode. FIG. 3 shows the device opened at the top, conforming on either side to a substrate (septum) 12. The device as shown in FIG. 3 shows the arms 10 flexed producing a force (F) (from the flexural modulus of the members) on the substrate (septum) 12. The soft ball material 11 (head) in contact with the substrate (septum) 12 distributes the force (F) and conforms to irregular surfaces. This eliminates any point contact forces that could be irritating and cause debilitating effects. The soft ball material 11 can be either cross linked-molecularly. Bonded with an adhesive or mechanically fixed to the force producing arms 10. The force (F) produced by the arms 10 and distributed by the soft ball 11 conforms to almost any regular or irregular surfaces such as the septum and causes a stimulation on the nerves of same. This stimulation force (F) could relieve problems with breathing, sleeping, snoring and nasal and eye secretions. FIG. 4 shows a configuration where the same attributes could be achieved by completely encompassing the pressure producting arms 13 with a soft material 14. The soft material 14 is the same material as 11 of FIGS. 1 and 2 above.

What is claimed:

1. A therapeutic device for stimulating nerves of the nasal septum and for being removably retained in a position in the nostrils of a person, whereby the positioned device is adapted to engage opposite sides of the nasal septum and to lie adjacent the nose portion anterior of the septum said septum having a thickened forward portion and a thinner inner portion, said device including;

a) a generally U-shaped element having first and second longitudinally extending opposing resilient arms lying in a common plane, each said arm having a free end and a connected end, and the arms having opposing inner surfaces, a transversely extending connecting portion that interconnects the connected ends of said arms, said connecting portion spaced a predetermined distance from the free ends of said arms and adapted to abut said anterior nose portion to limit inward movement of said device relative to the nostrils; and b) septum-engaging means on the free end of each resilient arm and insertable in the nostrils, said means providing a substantially spherical resiliently yieldable and conformal portion that projects inwardly from said arm inner surface and into close proximity to said yieldable portion of the other arm, in which position of close proximity the spacing between said yieldable portions is substantially less than the thickness of the septum, and whereby said arms are adapted to be resiliently spread apart in said plane to separate said septum-engaging means and resiliently urge said means towards their position of close proximity and whereby said substantially spherical portions are adapted to engage said septum inner portion and stimulate said septum inner portion with a predetermined amount of uniform compressive force.

2. A device as defined in claim 1 wherein said arms are generally straight and wherein said yieldable portions are adapted to conform to irregularities in said septum.

3. A device as defined in claim 1 wherein the connecting portion of said U-shaped element has an inner surface adapted to abut said nose anterior portion, and whereby said portion surface is spaced from the septum-engaging means by a distance of about one and a half the spacing between said opposing arm inner surfaces.

4. A device as defined in claim 1 wherein said septum-engaging means is comprised of soft plastic material and is adapted to resiliently conform to irregular surfaces and to distribute pressure evenly thereover.

5. A device as defined in claim 1 wherein said septum-engaging means comprises a spherical ball of soft plastic material, the center of each of said balls being substantially aligned with said inner surface of said arm.

6. A device as defined in claim 5 wherein each of said arms has an outer surface opposite said arm inner surface, and wherein said outer surface is substantially tangential to said ball.

* * * * *